United States Patent [19]

Grabos, Jr. et al.

[11] Patent Number: 5,363,512
[45] Date of Patent: Nov. 15, 1994

[54] PROTECTIVE GOGGLE AND LENS WITH ADJUSTABLE VENTILATION

[75] Inventors: Fred F. Grabos, Jr.; George V. Dondero, both of Ketchum, Id.

[73] Assignee: Smith Sport Optics, Inc., Ketchum, Id.

[21] Appl. No.: 828,434

[22] Filed: Jan. 30, 1992

[51] Int. Cl.$^5$ ............................................. A61F 9/02
[52] U.S. Cl. ............................................. 2/436; 2/441
[58] Field of Search .............. 2/436, 437, 431, 426, 2/9, 10, 171.3, 8, 424, 425, 441, 443

[56] References Cited

U.S. PATENT DOCUMENTS

| | | | |
|---|---|---|---|
| 2,537,275 | 1/1951 | Malcom, Jr. | 2/437 |
| 3,517,393 | 6/1970 | Beauchef | 2/436 |
| 3,663,959 | 5/1972 | Loubeyre | 2/436 X |
| 3,718,937 | 3/1973 | Smith | 2/436 |
| 3,945,044 | 3/1976 | McGee et al. | 2/436 |
| 4,149,276 | 4/1979 | Castro | 2/437 |
| 4,150,443 | 4/1979 | McNeilly | 2/436 |
| 4,571,748 | 2/1986 | Carroll et al. | 2/436 |
| 4,612,675 | 9/1986 | Broersman | 2/424 |
| 4,649,577 | 3/1987 | Wiedner | 2/437 X |
| 4,698,856 | 10/1987 | Arai | 2/425 |
| 4,868,929 | 9/1989 | Curcio | 2/435 |
| 4,964,178 | 10/1990 | Giancarlo et al. | 2/171.7 X |
| 4,977,627 | 12/1990 | Metcalfe et al. | 2/437 |
| 5,138,714 | 8/1992 | Smith | 2/9 |

FOREIGN PATENT DOCUMENTS

| | | | |
|---|---|---|---|
| 1343531 | 10/1963 | France | 2/436 |
| 0150848 | 9/1981 | Germany | 2/436 |
| 562924 | 7/1944 | United Kingdom . | |
| 930735 | 7/1963 | United Kingdom . | |

OTHER PUBLICATIONS

Smith Dealer Catalog 1990–1991, pp. 3 and 4 by Smith Sport Optics, Inc., Sun Valley, Id.

*Primary Examiner*—Peter Nerbun
*Attorney, Agent, or Firm*—Jenner & Block

[57] ABSTRACT

A ventilation adjustment assembly is provided for a goggle having a ventilated lens mounted in a frame. In one embodiment, the lens has one or more ventilation apertures forming a linear or curved path. An elongated shutter housing is formed by a base having pair of parallel sidewalls or spacers mounted on the lens on opposite sides of and in close proximity to the path of lens apertures. One or more apertures on the base align with the lens apertures. An elongated shutter is slidably disposed in the shutter housing. The shutter has one or more apertures which are alignable with apertures in the base and lens. By sliding the shutter within its housing, ventilation air flow is regulated as the shutter apertures move in and out of alignment with the base and lens apertures.

51 Claims, 3 Drawing Sheets

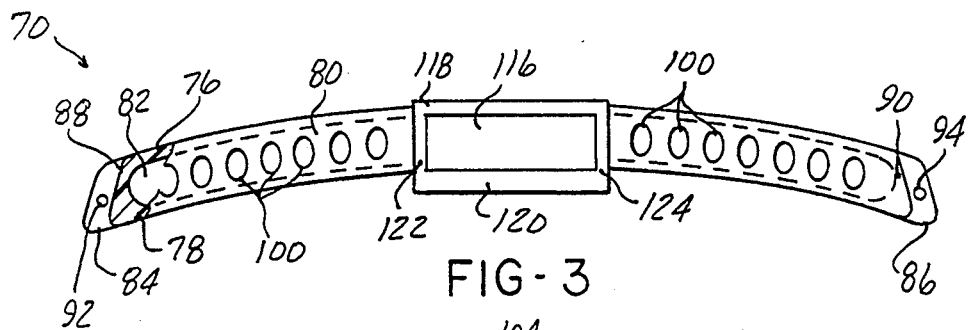

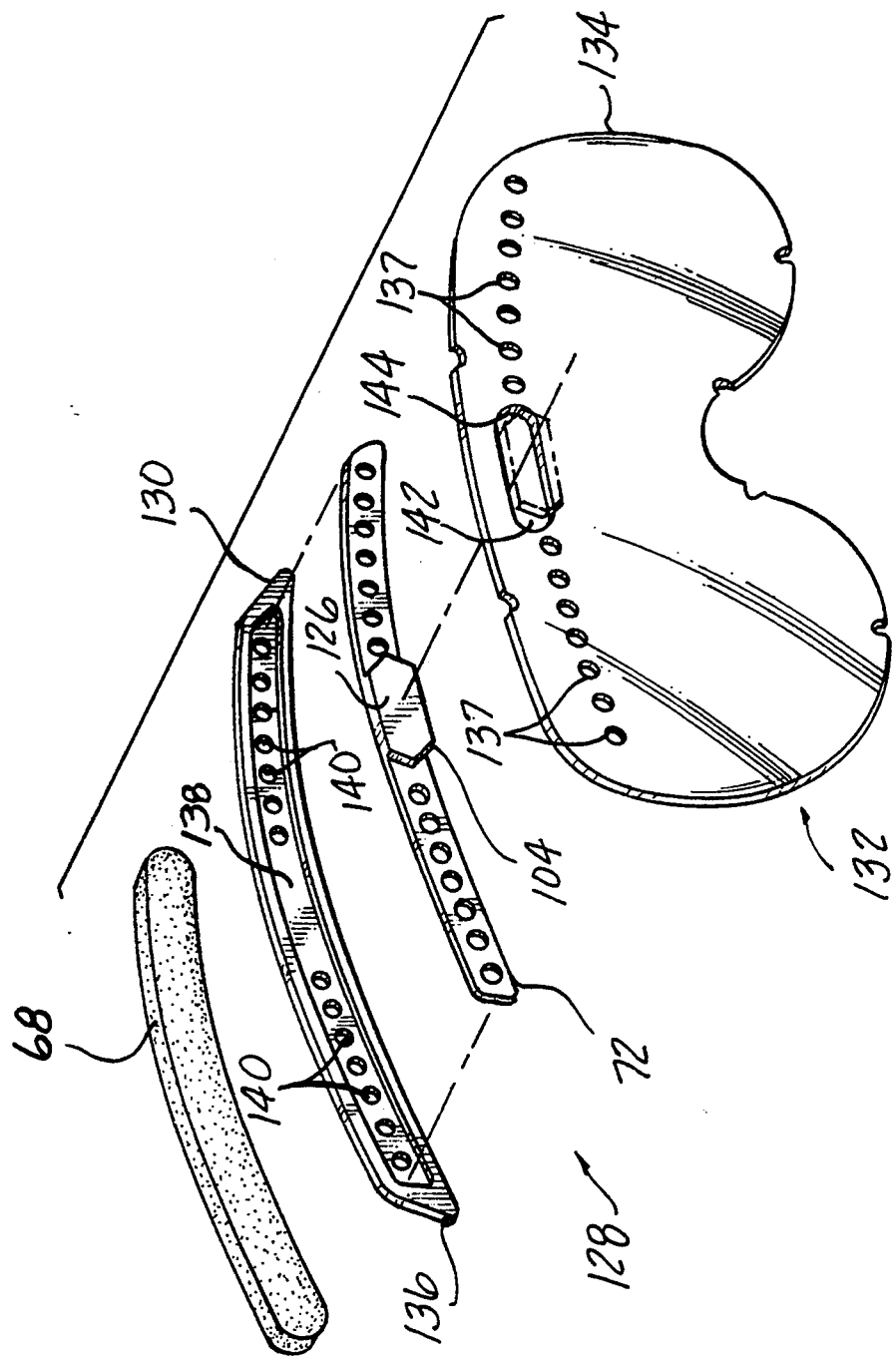

PROTECTIVE GOGGLE AND LENS WITH ADJUSTABLE VENTILATION

FIELD OF THE INVENTION

This invention relates generally to protective goggles having adjustable ventilation. More particularly, this invention relates to goggles which have a flexible lens housing and are particularly well-suited for use in skiing and other outdoor sports.

BACKGROUND OF THE INVENTION

Flexible goggles having a flexible housing in which a lens is mounted are well-known. Such goggles often use a thermal lens which includes two lenses spaced in parallel relation, such as by a closed cell foam spacer, to form an air-tight chamber between the two lenses for providing thermal insulation. Such goggles are commonly used by skiers and motorcyclists to protect their eyes from wind, precipitation and debris. They may also be used by surgeons and other medical personnel during operations and the like to protect eyes from fluids such as blood. The major drawback of conventional goggles is that condensation has a tendency to form on the inside of the lens thus fogging the lens and blocking the user's vision.

To prevent fogging, ski goggles have been provided with ventilating apertures which overcome the drawback of fogging, but which may, under some circumstances, allow excessive ventilation. This excessive ventilation results in a stream of cold air which may be unpleasant to the user, especially in extremely cold weather. Moreover, excessive ventilation can dry or otherwise damage sensitive tissue in and around the eyes. It has been proposed to control the passage of air by pivotable automatic flaps for closing an air passage opening when the user reaches a certain minimum speed. However, such devices are not practical, can be subject to icing of the closure mechanism, and are not manually adjustable by the user.

Ideally, a ventilation system for flexible goggles would be inexpensive to manufacture, manually adjustable and easy to operate. Ease of use is particularly important because users may often be wearing gloves or mittens which reduce their dexterity.

SUMMARY OF THE INVENTION

To overcome the deficiencies of the prior art, a goggle having adjustable ventilation is provided. In accordance with the invention, the goggle includes a frame in which a lens is mounted. The lens has one or more ventilation apertures. A ventilation adjustment assembly is mounted on the lens to regulate air flow through the ventilation aperture. The ventilation adjustment assembly uses a shutter or other suitable obstructing member which is movably disposed on the surface of the lens for being continuously positioned in and out of alignment with the lens' ventilation apertures.

In one embodiment, the lens has one or more ventilation apertures forming a linear or curved path. An elongated shutter housing is formed by a base having a pair of parallel sidewalls or spacers mounted on the lens on opposite sides of and in close proximity to the path of lens apertures. One or more apertures on the base align with the lens apertures. An elongated shutter is slidably disposed in the shutter housing. The shutter has one or more apertures which are alignable with apertures in the base and lens. By sliding the shutter within its housing, ventilation air flow is regulated as the shutter apertures move in and out of alignment with the base and lens apertures. A strip of permeable foam is placed over the lens ventilation apertures to baffle ventilation air flow.

The present invention provides an adjustable ventilation system which can be inexpensively manufactured from just two plastic parts (the shutter and the shutter housing). In the embodiments disclosed herein, a simple sliding motion of the shutter allows easy manual adjustment of ventilation airflow over a continuous range. This feature makes the invention particularly useful in outdoor sports such as skiing.

Also, because goggle lenses are typically removable for easy replacement, the invention may be embodied on a lens by itself. This allows the lens assembly which includes the manually adjustable ventilation system to be sold separately and as a replacement part for conventional goggles. Thus, a user can convert a standard goggle with a replaceable single or thermal lens into a goggle system having manually adjustable ventilation by purchases of the lens assembly alone and replacement of the original lens.

BRIEF DESCRIPTION OF THE DRAWINGS

FIG. 3 is a front elevation view of the shutter housing shown in FIG. 2;

FIG. 4 is a top plan view of the elongated apertured shutter shown in FIG. 2;

FIG. 5 is a diagram showing the ventilation adjustment assembly shown in FIG. 1 with the shutter in a fully closed position;

FIG. 6 is a diagram showing the ventilation adjustment assembly shown in FIG. 1 with the shutter in a fully opened position;

FIG. 7 is a sectional view of the ventilation adjustment assembly taken along lines 7—7 in FIG. 5;

FIG. 8 is a sectional view of the ventilation adjustment assembly taken along lines 8—8 in FIG. 6; and FIG. 9 is a partial exploded view of a goggle in accordance with a second embodiment of the invention.

DETAILED DESCRIPTION OF THE PREFERRED EMBODIMENTS

Figure 1:
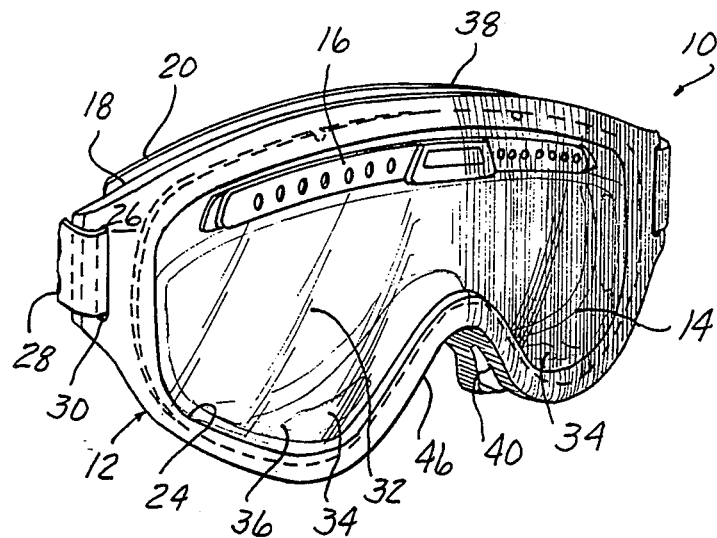
FIG. 1 is a perspective view of a goggle in accordance with the invention.

Turning now to the drawings in which similar reference characters denote similar elements throughout the several views, FIG. 1 is a perspective view of a goggle 10 in accordance with the invention. Goggle 10 generally comprises a frame 12, a lens structure 14 which is mounted in the frame 12, and a ventilation adjustment assembly 16 which is mounted on the lens structure 14.

Goggle frame 12 may have a generally annular structure and may be molded of one piece from a resilient flexible material such as a soft plastic or soft rubber. A face contacting flange or rim 18 is lined with a padding or cushion 20 of sponge-type material to seal frame 12 against the user's face (not illustrated). Lens structure 14 of flexible transparent material (which may be colored if desired) has a peripheral edge 22 which is received within a peripheral groove 24 formed interiorly around a front section 26 of frame 12. Lens structure 14 may be flat and bent to an arcuate configuration which fits frame 12, or may be curved and could, if desired, form a part of the structural support to maintain the shape of goggle 10.

To secure goggle 10 to the user's head, an elastic headband or strap 28 has folded, stitched ends which are received in slots 30 formed in frame front section 26. A slide buckle (not illustrated) allows adjustment of the length of elastic strap 28.

Goggle 10 is shaped to fit flush against the contours of the human face. Consequently, when worn by a user, a generally closed chamber 32 is located between lens structure 14 and the user's face (not illustrated). The user's body heat and evaporating perspiration cause moisture to condense inside chamber 32. Some of this condensation collects on the inside surface of lens structure 14 fogging lens structure 14 and thereby reducing the user's vision.

It is known that ventilation can reduce this problem. For example, goggle frame 12 may have a plurality of large vent openings 34 formed by ribs 36 which join the rim 18 to the front section 26. On the exterior side, the ribs 36 define with the rim 18 and front section 26 a channel 38 for a fibrous or open cell foam lining 40 which covers the openings 34 to allow a slow exchange of air between the goggle exterior and the closed chamber 32. While lining 40 is moisture and air permeable, it blocks snow and the like from entering chamber 32.

Other conventional ventilation systems, however, may be utilized in place of the illustrated vent apertures covered by a fibrous strip. While helpful, the ventilation provided by such systems is typically either insufficient to prevent fogging of lens structure 14 or so great as to cause the user discomfort. The goggle structure described above (excluding ventilation adjustment assembly 16) is well-known, and various modifications may be made thereto as desired.

Figure 2:
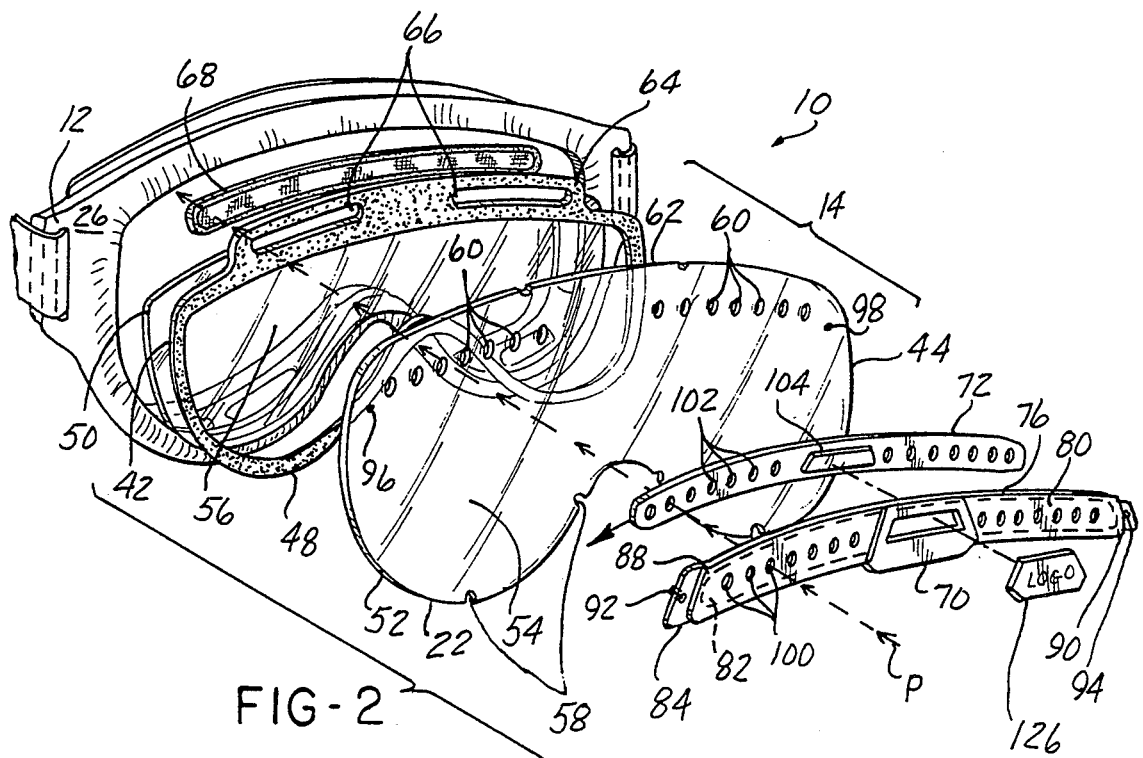
FIG. 2 is an exploded perspective view of the goggle shown in FIG. 1.

Referring to FIG. 2, lens structure 14 is illustrated in greater detail. In a preferred embodiment, the lens structure 14 is a so-called thermal lens, although the invention may be implemented with a single lens or other types of lenses. Lens structure 14 is formed of an inner lens 42 and an outer lens 44, both stamped from a generally planar sheet of transparent, semirigid plastic, the sheet being of uniform thickness. As best seen in FIG. 1, lenses 42 and 44 are horizontally elongated and intermediate their ends each is provided with a downwardly opening recess 46 to accommodate the nose of a wearer.

Lenses 42 and 44 are assembled and spaced in parallel relation by an interconnecting spacer 48. Interconnecting spacer 48 is made of closed cell, flexible foam which is bonded to lenses 42 and 44 in any suitable fashion so as to seal against both. Interconnecting spacer 48 is located in close proximity to peripheral edges 50 and 52 of lenses 42 and 44, respectively, and extends peripherally thereabout to define a central viewing area 54. Because interconnecting spacer 48 seals against both lenses 42 and 44, a space or chamber 56 between such lenses and central viewing area 54 is sealed to provide the thermal lens. It will be observed that lenses 42 and 44 can be integrally joined to define sealed space 56 between and inner and outer lens surfaces.

Lens structure 14 is deformed from the plane of the plastic sheets making up lenses 42 and 44 into a simple curve, as opposed to a compound curve. That is, for all horizontal sections taken through lens structure 14 at any point thereon, the curve will have essentially the same profile. Stated another way, the lens is curved only about its minor dimension and not about both minor and major dimensions.

Outer lens 44 is of a size and shape suitable for mounting lens structure 14 in front section 26. A plurality of keyholes 58 along periphery 52 of outer lens 44 engage corresponding fingers (not illustrated) in peripheral groove 24 of frame front section 26 to releasably secure outer lens 44 therein.

In accordance with the invention, outer lens 44 also has a plurality of evenly spaced apertures 60 for ventilating chamber 32. Apertures 60 may be of uniform size, spacing and circular shape and the distance between each of apertures 60 exceeds their individual width or diameter. The invention may also be practiced using apertures of irregular size, shape and spacing, or using only a single aperture. Apertures 60 are generally in linear alignment, although they may define a path that is somewhat curved about an axis running perpendicular to the plane of outer lens 44. Apertures 60 are arranged in a horizontal orientation near top edge 62 of outer lens 44. Apertures 60 need not be provided near the middle portion of outer lens 44.

Foam spacer 48 and inner lens 42 are somewhat shorter than outer lens 44, so that apertures 60 are outside the area encircled by foam spacer 48 and are, therefore, not obstructed by inner lens 42. It will be observed that this construction permits the use of ventilation apertures in a thermal lens without puncturing sealed space 56. An elongated tab 64 also constructed of closed cell foam extends upwardly from spacer 48 and is mounted to the region of outer lens 44 containing the plurality of apertures 60. Two slotted apertures 66 in elongated tab 64 are positioned behind apertures 60 to permit the movement of ventilation air therethrough.

An elongated open cell foam filter 68 is horizontally orientated and is mounted on and in alignment with tab 64. Open cell foam filter 68 serves to filter air streaming through ventilation apertures 60 and slotted apertures 66, thereby preventing the intrusion into chamber 32 of particles or droplets of precipitation such as rain or snow, for example. Open cell foam filter 68 also serves to baffle ventilation air flow having an otherwise excessive velocity.

As best seen in FIGS. 1 and 2, ventilation adjustment assembly 16 is located over the plurality of apertures 60 on outer lens 44 to regulate the flow of air therethrough. It will be noted that ventilation adjustment assembly 16 is mounted near the periphery of central viewing area 54 so as to minimize interference with the user's vision. Ventilation adjustment assembly 16 comprises a three-sided shutter housing or slide 70 in which an elongated shutter 72 is slidably disposed. As discussed below in greater detail, shutter housing 70 is mounted on lens 44 over apertures 60 to create a channel thereover. A thin, elongated apertured shutter 72 or other suitable obstruction member is slidably disposed in this channel, and various positions of the shutter 72 allow more or less ventilating air to pass through lens apertures 60. Shutter housing 70 and shutter 72 may be slightly arcuate to accommodate the curvatures of lens 44 and the path of alignment of apertures 60.

Referring to FIGS. 2 and 3, the shutter housing 70 has a three-sided cross-section formed by a pair of thin, parallel spacers or sidewalls 76 and 78 mounted on lens 44 and a relatively wider cover 80 which is mounted onto the sidewalls 76 and 78. Sidewalls 76 and 78 are positioned on opposite sides of the line of apertures 60 in lens 44. Lens 44, sidewalls 76 and 78, and cover 80 define a channel or track 82 extending over the apertures 60 along the width of outer lens 44. Flanges 84 and 86 are attached to opposite longitudinal ends 88 and 90, respectively, of shutter housing cover 80 for mounting cover 80 to the lens 44. Index posts or fingers 92 and 94 extend outwardly from flanges 84 and 86, respectively, and are received by index apertures 96 and 98 in lens 44. Sidewalls 76 and 78 and flanges 84 and 86 are mounted to lens 44 by solvent bonding.

Shutter housing cover 80 has a plurality of apertures 100 of substantially the same number, size and spacing as the apertures on lens 44. Shutter housing 70 is mounted so that apertures 100 on cover 80 are substantially in alignment with apertures 60 on lens 44. Apertures 100 may have an oval shape with their respective elongated axes generally perpendicular to the elongated length of shutter housing 70. Goggle 10 could be constructed (not shown) without shutter housing cover 80 using only sidewalls 76 and 78 to form a channel, such as channel 82, as long as sidewalls 76 and 78 would not cover apertures 102 of shutter 72 to an undesirable degree.

As best seen in FIG. 2, a ventilation path for air flow extends along path P through apertures 100 on shutter housing cover 80, apertures 60 on lens 44, slotted apertures 66 on elongated tab 64 and the open cell foam filter 68. It will be observed that a person wearing goggle 10 tends to face his or her direction of travel, as is typical. Because a person wearing goggle 10 can travel at a relatively high rate of speed through cold winter air, such as with skiing or snowmobiling, cold air can be forced through path P and into chamber 32 at a velocity to cause the person some discomfort. Therefore, it is desirable to regulate the flow of air through apertures 100, as well as to control the amount of airflow for different fogging conditions which will depend on atmospheric conditions.

In accordance with the present invention, regulation of ventilation air flow along path P is provided by elongated shutter 72 which is slidably disposed inside of channel 82 of shutter housing 70. Shutter 72 is curved to follow the path of alignment of apertures 60 on outer lens 44 and the contours of channel 82. A plurality of apertures 102 are spaced along the elongated length of shutter 72. The apertures 102 are substantially identical in size, shape, and spacing to the apertures 100 on shutter housing cover 80, but may also be slightly smaller in size or fewer in number.

FIGS. 5 and 6 show an assembled ventilation adjustment assembly in closed and open positions, respectively. As illustrated by the arrows, shutter 72 may be slidably positioned to bring apertures 102 on shutter 72 in and out of alignment with apertures 100 on shutter housing cover 80. When shutter apertures 102 are completely aligned with shutter housing cover apertures 100 (as shown in FIG. 6) apertures 100 are unobstructed, and ventilation air flows freely along path P (see FIG. 2). As shutter apertures 102 are moved out of alignment with shutter housing cover apertures 100, air flow through apertures 100 is progressively obstructed. When shutter apertures 102 are completely out of alignment with apertures 100 (as shown in FIG. 5), apertures 100 are completely obstructed, and no ventilation air flows along path P. It will be noted that the spaces between each of apertures 100 (and apertures 102) must be at least as wide as the apertures themselves. In this manner, the portions between apertures 102 of shutter 72 will be sufficiently wide to completely block apertures 100.

Referring to FIG. 4, elongated shutter 72 has a raised region 104 located at the midsection of shutter 72. Raised region 104 comprises four raised edges 106, 108, 110 and 112 which circumscribe a rectangular void 114. Rectangular void 114 serves to reduce the cost of manufacturing shutter 72 by eliminating the plastic or like material which would otherwise fill void 114. Alternatively, raised region 104 may be solid.

As best seen in FIGS. 2-3, shutter 72 is disposed in channel 82 so that raised area 104 projects outwardly through an aperture or collar 116 in shutter housing cover 80. Aperture 116 is generally rectangular in shape and is circumscribed by braces 118 and 120 and stops 122 and 124. Braces 118 and 120 are superimposed on sidewalls 76 and 78, respectively. Braces 118 and 120 may be slightly thicker and wider than sidewalls 76 and 78, and serve to strengthen shutter housing cover 80 along the length of aperture 116. Without the braces 118 and 120, shutter housing cover 80 tends to buckle at a point along aperture 116 when flexible frame 12 is bent.

Stops 122 and 124 are slightly thicker than shutter housing cover 80, and serve to define the range within which shutter 72 is slidable, as discussed below. Raised region 104 should protrude slightly past braces 118 and 120 and stops 122 and 124. A generally rectangular plate 126 (shown in FIGS. 2, 5, and 6) is mounted flat onto raised region 104. Rectangular plate 126 serves as a manual adjustment button or knob by which the user's finger can engage shutter 72 for sliding motion within channel 82. Plate 126 is larger in area than raised area 104 and may have longitudinal edges 127 and 129 which overhang braces 118 and 120, respectively, as shown in FIG. 5. The surface of plate 126 has ridges (not illustrated) which can be shaped into raised letters of a trade name or logo. These ridges provide the user's finger with a better gripping surface when engaging plate 126.

Referring to FIGS. 5-8, the operation of ventilation adjustment assembly 16 may be more thoroughly understood. For clarity, FIGS. 5 and 6 depict an assembled ventilation adjustment assembly. Consequently, plate 126 is positioned over raised area 104, which is therefore not shown. It should be understood that while plate 126 and aperture 116 and void 114 are depicted as plain rectangles in FIGS. 3-6, in practice, aesthetic considerations might dictate the use of more stylized designs, such as depicted in FIG. 2, and that the invention fully contemplates the use of such alternative designs.

Shutter 72 fits snugly in channel 82. In this manner (and particularly when shutter housing 70 and shutter 72 are curved), the sides of shutter 72 will impinge the interior walls of channel 82. This contact creates a friction force which tends to restrain movement of shutter 72 and keep shutter 72 in a fixed position within channel 82 until the wearer physically changes the position of shutter 72 as hereinafter described.

When the user's finger engages plate 126 and applies a force in a direction parallel to the surface of plate 126 which is sufficient to overcome the frictional resistance, shutter 72 is slidably moved in that direction in channel 82 to open, partially close, or close apertures 60. It will be observed that braces 118 and 120 of shutter housing cover 80 slidably engage with edges 108 and 112, respectively, of raised region 104, as the user slides plate 126 and shutter 72 back and forth.

As shown in FIGS. 7 and 8, front plate 126 is integrally connected to shutter 72 by edges 106 and 110 of raised region 104. Referring to FIGS. 5 and 7, a user may, by engaging front plate 126, slide shutter 72 toward end 88 of shutter housing cover 80 until edge 106 of raised region 104 abuts stop 122. Likewise, as shown in FIGS. 6 and 8, shutter 72 may be slid toward end 90 of shutter housing cover 80 until edge 110 of raised region 104 abuts stops 124. In this manner, the spacing between backstop 122 and 124 determines the range of lateral movement of shutter 72. Stops 122 and 124 are spaced sufficiently apart to allow shutter 72 a range of movement greater than the width of apertures 100, but less than the distance between each of apertures 100. This range is just sufficient to allow movement of shutter 72 from the fully closed position of FIG. 5 to the fully open position of FIG. 6.

Apertures 102 are then positioned on shutter 72 so that when shutter 72 is at one extreme of its range of sliding movement, shutter apertures 102 are substantially in alignment with shutter housing cover apertures 100. When shutter 72 is positioned at the opposite extreme of its range of sliding movement, shutter apertures 102 should be completely out of alignment with shutter housing cover apertures 100. Shutter 72 may also be placed at intermediate positions on its range of sliding movement to place shutter apertures 102 in partial alignment with shutter housing cover apertures 100.

For example, in FIGS. 5 and 7, shutter 72 has been slid toward shutter housing cover end 88 until edge 106 abuts stop 122. In this position, each shutter aperture 102, such as aperture 102 in FIG. 7 is out of alignment with its corresponding shutter housing cover aperture 100. In FIG. 7, aperture 100 is completely blocked, and no ventilation air flows through aperture 100 or any other apertures 100, which are all similarly blocked.

In comparison, as seen in FIGS. 6 and 8, shutter 72 has been slid toward shutter housing cover end 90 until edge 110 of raised region 104 abuts stop 124. In this position, each shutter hole 102 is in complete alignment with its corresponding shutter housing cover hole 100. Thus, each shutter housing cover hole 100 is unobstructed by shutter 72, and ventilation air flows freely through apertures 100 each of which is also unobstructed.

In addition, the shutter 72 may be left in some intermediate position, thereby providing a continuous range of adjustability for ventilation air flow through apertures 100 and into chamber 32. In this manner, a user may manually engage plate 126 to position shutter 72 so that the precisely desired level or ventilation is received into chamber 32.

Various changes can be made to the illustrated embodiments. For example, lens 44 could have only one ventilation hole (as opposed to a plurality). Lens ventilation apertures 60 could be vertically oriented. Ventilation apertures of different or irregular shape, size, and spacing could be used in lens 44, so long as the apertures in shutter housing cover 80 and shutter 72 are alignable therewith. Shutter housing 70 can be replaced by other suitable devices for slidably mounting shutter 72 on lens 44, including grooves in the lens itself for slidably receiving shutter 72. Alternatively, shutter 72 can be mounted between portions of inner lens 42 and outer lens 44 which extend beyond the perimeter of foam spacer 48. Additionally, shutter 72 can be adapted for discrete (as opposed to continuous) movement in channel 82, such as by using detents or the like. Shutter housing cover 80 could be replaced by a plurality of cross members (not illustrated) spanning parallel sidewalls 76 and 78 to capture sliding shutter 72 therebetween. Shutter 72 may also be of any suitable shape and may be mounted for rotating (or opposed to slidable) movement relative to the surface of lens structure 14. Shutter 72 need not be in direct contact with the lens surface, and could, for example, be mounted in spaced relation to the lens surface.

As indicated above, lens structure 14 is removable from goggle 10 for easy replacement. Consequently, the lens structure 14 which includes ventilation adjustment assembly 16 may be sold separately and as a replacement part for conventional goggles. A user may convert a standard goggle with a replaceable single or thermal lens into a goggle such as goggle 10 having adjustable ventilation by purchasing lens structure 14 alone and replacing the user's original lens.

Referring to FIG. 9, an exploded view of a goggle 128 employing a second embodiment of the invention is provided. Goggle 128 is similar to the goggle 10 described above, and those parts of goggle 128 that differ from goggle 10 are illustrated in FIG. 9. Goggle 128 includes a ventilation adjustment assembly 130 mounted on a lens structure 132. Lens structure 132 is substantially identical to lens structure 14, and includes an outer lens 134 having a plurality of evenly spaced ventilation apertures 137. (For clarity, while a number of ventilation apertures 137 are shown, only four are indicated by a reference numeral.)

Ventilation air flow through apertures 137 is regulated by ventilation adjustment assembly 130. In goggle 128, the ventilation adjustment assembly 130 is mounted on the inside surface (i.e., that surface of the lens structure which faces a person wearing goggles 10) of the outer lens 134, as best seen in FIG. 9. Mounting the ventilation adjustment assembly 130 on the inside surface of lens structure 132 subjects housing 136 to certain compression (as opposed to tension) forces when goggle 10 is bent or flexed. It has been found that housing 136 more easily withstands these compression forces. Ventilation adjustment assembly 130 includes a three-sided shutter housing 136 which is mounted behind outer lens 134 over apertures 137. Shutter housing 136 includes a shutter housing cover 138 having a plurality of ventilation apertures 140. The elongated open cell foam filter 68 may be mounted over apertures 140 to filter air streaming therethrough. Because shutter housing 136 resides behind outer lens 134, it occupies the space which, in goggle 10, is occupied by tab 64. Therefore, goggle 128 need not includes a tab such as tab 64.

The thin, elongated shutter 72, described above in connection with goggle 10, is disposed in shutter housing 136 in the manner described above in connection with shutter housing 70. Raised area 104 of shutter 72 is disposed behind outer lens 134 so that raised area 104 projects outwardly through an aperture 142 in outer lens 134. Aperture 142 performs the same function as aperture 116 of shutter housing cover 80. The periphery 144 of aperture 142 corresponds in function to the braces 118 and 120 and stops 122 and 124 of shutter housing cover 80. Front plate 126 is integrally connected to shutter 72 as described above, to serve as a button or knob by which the user's finger can engage shutter 72 for sliding motion within shutter housing 136.

It will be observed that while shutter housing 136 is mounted on the inside surface of outer lens 134, the orientation of shutter 72 is the same in both goggle 10 and goggle 128. Consequently, shutter housing 136 has no central aperture, such as aperture 116, for receiving raised area 104 of shutter 72. Instead, raised area 104 projects through aperture 142 in outer lens 134.

Other modifications which can be made within the scope of the present invention will be understood in view of the foregoing. It is desired not to limit the invention to the embodiments illustrated as it will be apparent that a number of modifications can be made therein.

In the claims:

1. A goggle having adjustable ventilation, comprising:
   a frame having releasable lens mounting means and an annular structure defining a viewing area;
   a lens releasably mounted in said lens mounting means and having a ventilation aperture formed in said lens; and
   obstructing means connected to said lens adjacent to the surface of said lens for selectively obstructing said ventilation aperture formed in said lens.

2. The goggle according to claim 1 wherein said obstructing means includes a shutter and a slide wherein said shutter is slidably disposed in said slide.

3. The goggle according to claim 2 wherein said slide is mounted on said lens to superimpose said lens ventilation aperture.

4. The goggle according to claim 1 wherein said lens mounting means is an interior groove located in said annular frame structure for releasably receiving the peripheral edge of said lens to allow replacement of said lens.

5. The goggle according to claim 1 wherein said lens is a thermal lens having inner and outer lens surfaces in spaced parallel relation and a foam spacer which defines an annular viewing area, said foam spacer being disposed between said inner and outer lens surfaces to define a sealed chamber between said inner and outer lens surfaces, wherein said lens aperture extends through at least one of said inner and outer lens surfaces in a position outside of said viewing area so as not to penetrate said sealed chamber.

6. The goggle according to claim 1 wherein said obstructing means comprises an adjustment member projecting outwardly from said obstructing means for movement by the wearer of the goggle.

7. The goggle according to claim 6 wherein said obstructing means is disposed adjacent to the inside surface of said lens, and said lens further comprises a second aperture through which said adjustment member projects.

8. The goggle according to claim 1 wherein said lens ventilation aperture is located near the periphery of said viewing area.

9. A goggle having adjustable ventilation comprising:
   a goggle assembly including a frame defining a viewing area and a lens mounted in said frame over said viewing area, said goggle assembly further including spaced apart first and second ventilation apertures formed in said goggle assembly;
   first and second shutter portions suitable for obstructing air flow through said ventilation apertures;
   means for adjustably mounting said first and second shutter portions adjacent to said first and second ventilation apertures, respectively, to selectively obstruct said first and second ventilation apertures; and
   master adjustment means linked to both of said first and second shutter portions for manually adjusting both of said first and second shutter portions.

10. The goggle according to claim 9 wherein said mounting means includes a channel in which said first and second shutter portions are disposed, said channel being sized to snugly receive said first and second shutter portions to provide a friction fit tending to maintain said first and second shutter portions in a stationary position within said channel.

11. The goggle according to claim 9 wherein said first and second ventilation apertures are located in said lens.

12. The goggle according to claim 9 wherein said first shutter portion has an aperture movable relative to said goggle assembly for positioning in and out of alignment with said first ventilation aperture.

13. The goggle according to claim 9 wherein said first ventilation aperture includes a plurality of ventilation apertures forming a path along the surface of said goggle assembly;
   said second ventilation aperture includes a plurality of ventilation apertures forming a second path along the surface of said goggle assembly; and
   said first and second shutter portions superimpose said first and second paths of apertures, respectively, and wherein said first and second paths are spaced apart from each other.

14. The goggle according to claim 9 wherein said first and second apertures are located on the goggle so that when the goggle is worn, the first and second apertures are on opposite sides of the wearer's nose.

15. The goggle according to claim 9 wherein said first ventilation aperture is a plurality of first ventilation apertures forming a path along the surface of said goggle assembly, and said first shutter portion has a plurality of apertures which can be positioned in and out of alignment with said first ventilation apertures.

16. The goggle according to claim 9 wherein said mounting means comprises a shutter housing having a pair of spacers mounted on said goggle assembly on opposite sides and in close proximity to said first and second ventilation apertures to define said channel between said spacers.

17. The goggle according to claim 16 wherein said mounting means further comprises a cover bridging said spacers.

18. The lens structure according to claim 17 wherein said cover further comprises a cover ventilation aperture which is in at least partial alignment with said one of said first and second ventilation apertures.

19. The goggle according to claim 9 wherein said master adjustment means is an adjustment member projecting outwardly from said first and second shutter portions for movement by the wearer of the goggle.

20. The goggle according to claim 19 wherein said first and second shutter portions are adjacent to the inside surface of said goggle assembly, and said goggle assembly includes an adjustment aperture through which said adjustment member projects.

21. The lens structure according to claim 9 wherein said mounting means is integral to said goggle assembly.

22. A lens structure suitable for mounting in a goggle having a frame with a mounting structure for releasably receiving the lens structure, comprising:
   a lens having a lens ventilation aperture formed in the lens and a peripheral mounting structure for releasably mounting said lens to the frame;
   means for obstructing said lens ventilation aperture; and
   obstruction mounting means attached to the surface of said lens for adjustably mounting said obstructing means in close proximity to said lens ventilation aperture.

23. The lens structure according to claim 22 wherein said lens comprises an inner lens connected in spaced relation to an outer lens by an annular foam spacer to define a sealed chamber therebetween, wherein at least one of said inner and outer lenses includes a portion which extends beyond said annular foam spacer, wherein said lens ventilation aperture is located in said portion so as not to penetrate said sealed space.

24. The lens structure according to claim 23 further comprising an air permeable filter which covers said lens ventilation aperture.

25. The lens structure according to claim 22 wherein said obstructing means has a further aperture movable relative to said lens for positioning said further aperture in and out of alignment with said lens ventilation aperture.

26. The lens structure according to claim 22 wherein said lens has a plurality of lens ventilation apertures forming a path along the surface of said lens.

27. The lens structure according to claim 26 wherein said obstructing means is elongated and is disposed in said mounting means to superimpose said path of lens ventilation apertures.

28. The lens structure according to claim 27 wherein said obstructing means has a plurality of apertures which can be positioned in and out of alignment with said lens ventilation apertures.

29. The lens structure according to claim 22 wherein said obstructing means includes a shutter adjustably mounted on the surface of said lens.

30. The lens structure of claim 30 wherein said mounting means comprises a channel wherein said shutter member is slidably disposed.

31. The lens structure according to claim 30 wherein said channel is mounted on the surface of said lens so that said shutter disposed therein superimposes said lens ventilation aperture.

32. The lens structure according to claim 30 wherein said channel is sized to snugly receive said shutter for holding said shutter with a friction fit.

33. The lens structure according to claim 30 wherein said mounting means comprises a shutter housing having a pair of spacers mounted on said lens on opposite sides and in close proximity to said lens ventilation aperture to define said channel.

34. The lens structure according to claim 33 wherein said mounting means further comprises a cover bridging said spacers.

35. The lens structure according to claim 34 wherein said cover further comprises a cover ventilation aperture.

36. The lens structure according to claim 35 wherein said cover ventilation aperture is aligned with said lens ventilation aperture.

37. The lens structure according to claim 34 wherein said cover includes an adjustment aperture, and wherein said shutter includes an adjustment member extending from said shutter through said cover adjustment aperture for movement of said shutter by a wearer of the goggle.

38. The lens structure according to claim 37 wherein said adjustment aperture is sized to allow limited movement of said adjustment member therein.

39. The lens structure according to claim 22 further comprising an adjustment member projecting outwardly from said obstructing member.

40. The lens structure according to claim 39 wherein said adjustment member has at its distal end a ridge bearing surface for manual engagement by a person wearing the goggle.

41. The lens structure according to claim 39 wherein said obstructing member is disposed on the inside surface of said lens, and wherein said lens has a second aperture through which said adjustment member extends.

42. The lens structure according to claim 41 wherein said second lens aperture is sized to allow limited relative movement of said adjustment member therein.

43. A lens structure suitable for mounting in a goggle having a frame with a mounting structure for releasably receiving the lens, comprising:
 a lens having an outer lens portion, an inner lens portion, and a ventilation aperture through said lens;
 spacer means for interconnecting said first and second lens portions to define a sealed chamber therebetween;
 a mounting structure for mounting said lens structure to the frame;
 means for obstructing said lens ventilation aperture;
 a slide mounted to the surface of said lens structure having a channel superimposed with said lens ventilation aperture, wherein said obstructing means is slidably disposed in said channel; and
 an adjustment member extending from said obstructing means for engagement by the wearer of the goggle.

44. The lens structure according to claim 43 wherein said lens further comprises a flange extending beyond the periphery of said sealed chamber, wherein said lens aperture is located in said flange.

45. The lens structure according to claim 44 wherein said flange extends from at least one of said inner and outer lens portions, and said slide is mounted on the surface of said flange.

46. The lens structure according to claim 44 wherein said flange has a further aperture through which said adjustment member extends.

47. The lens structure according to claim 43 wherein said obstructing means is an elongated shutter.

48. The lens structure according to claim 47 wherein said shutter includes an aperture movable fir alignment with said lens ventilation aperture.

49. The lens structure according to claim 43 wherein said slide is integral with said lens.

50. A goggle having adjustable ventilation, comprising:
 a frame;
 a lens mounted in said frame and having a ventilation aperture and an adjustment aperture formed in the lens;
 means movably disposed adjacent to an inside surface of said lens for selectively obstructing said lens ventilation aperture, said obstructing means including an adjustment member projecting outwardly through said adjustment aperture for movement by the wearer of the goggle;
 wherein said obstructing means comprises a further aperture formed therein movable relative to said lens for positioning said further aperture in at least partial alignment with said lens aperture.

51. The goggle according to claim 1 wherein said obstructing means includes a further aperture formed therein movable relative to said lens for positioning said further aperture in at least partial alignment with said lens aperture.

* * * * *